US 6,464,717 B1

(54) BRA WITH HOT/COLD INSERTS

(76) Inventors: Gairy L. Smith, 290 Victoria St., Apartment C-1, Costa Mesa, CA (US) 92627; Pierre Scales, 2730 Fauna Ct., Merced, CA (US) 95340; Donna Rucker, 2023 O St. Apt 14, Merced, CA (US) 95340

( * ) Notice: Subject to any disclaimer, the term of this patent is extended or adjusted under 35 U.S.C. 154(b) by 19 days.

(21) Appl. No.: 09/615,093

(22) Filed: Jul. 12, 2000

Related U.S. Application Data

(60) Provisional application No. 60/149,476, filed on Aug. 19, 1999.

(51) Int. Cl.[7] .................................................. A61F 7/00
(52) U.S. Cl. ........................ 607/108; 607/112; 607/114; 450/58
(58) Field of Search ............................ 607/108, 96, 112, 607/114; 602/14, 19, 62; 450/58, 54, 37, 32, 55, 79, 38, 89

(56) References Cited

U.S. PATENT DOCUMENTS

| | | |
|---|---|---|
| 2,298,361 A | 10/1942 | Freund |
| 3,326,218 A | 6/1967 | McAlphine |
| 3,995,621 A | 12/1976 | Flectcher et al. |
| 5,032,104 A * | 7/1991 | Rainville ........................ 2/101 |
| 5,050,595 A | 9/1991 | Krafft |
| 5,188,585 A * | 2/1993 | Peters ...................... 128/100.1 |
| 5,235,974 A | 8/1993 | Miller |
| 5,304,215 A | 4/1994 | MacWhinnie et al. |
| 5,441,534 A | 8/1995 | MacWhinnie et al. |
| 5,507,794 A * | 4/1996 | Allen .......................... 126/204 |
| 5,679,052 A | 10/1997 | Rucki |
| 5,690,537 A * | 11/1997 | Kalmus .......................... 2/267 |
| 5,897,580 A * | 4/1999 | Silver .......................... 128/889 |
| RE36,869 E * | 9/2000 | Ewen ............................ 2/102 |
| 6,135,975 A * | 10/2000 | Johnstone ..................... 602/19 |

FOREIGN PATENT DOCUMENTS

| | | |
|---|---|---|
| DE | 4141806 | 5/1993 |

* cited by examiner

*Primary Examiner*—Linda C. M. Dvorak
*Assistant Examiner*—Kenneth G. Schopfer
(74) *Attorney, Agent, or Firm*—Richard C. Litman

(57) ABSTRACT

The bra with hot/cold inserts is a therapeutic device in the form of a vest-like elastic garment adapted to be worn on the human upper torso. The device includes front panels having pockets therein for retaining gel packs. The device is effective in providing warm or cold therapy to the chest and rib areas. The garment can be used by humans of both genders.

5 Claims, 2 Drawing Sheets

BRA WITH HOT/COLD INSERTS

CROSS-REFERENCE TO RELATED APPLICATION

This application claims the benefit of U.S. Provisional Patent Application Ser. No. 60/149,476, filed Aug. 19, 1999.

BACKGROUND OF THE INVENTION

1. Field of the Invention

The present invention relates generally to wearing apparel. More specifically, the present invention is drawn to a vest-like garment having pockets to accommodate hot or cold thermal packs.

2. Description of Related Art

The prior art discloses many garments which, when worn, are designed to heat or cool specific parts of the human torso. For example, brassieres using a circulated fluid to cool or heat the breasts are disclosed in U.S. Pat. No. 2,298,361 (Freund), U.S. Pat. No. 3,326,218 (McAlpine), and U.S. Pat. No. 3,995,621 (Fletcher et al.).

U.S. Pat. No. 5,235,974 (Miller) shows a brassiere heated by electric means.

U.S. Pat. No. 5,050,595 (Krafft), U.S. Pat. No. 5,304,215 (McWhinnie et al.), U.S. Pat. No. 5,441,534 (McWhinnie et al.), U.S. Pat. No. 5,679,052 (Rucki), and German Patent No. 4,141,806 disclose thermal packs adapted to be applied directly to a woman's breast.

None of the above inventions and patents, taken either singly or in combination, is seen to disclose a sturdily constructed, therapeutic, thermal vest designed for use by both genders as will subsequently be described and claimed in the instant invention.

SUMMARY OF THE INVENTION

The present invention, dubbed "Thermal Vest", comprises a garment fabricated from a sturdy material which is adapted to be comfortably worn by both males and females. Configured to accommodate a wide range of sizes, the vest is highly effective for treatment of numerous upper torso physical conditions which require warm or cold therapy.

The vest is provided with pockets to accommodate gel packs, which packs may be heated or chilled to achieve the desired result. The vest includes an outer layer made of a material which has an elastic ability to distribute pressure evenly across the upper human torso. The outer layer is breathable and has good insulation qualities. A soft, skin-friendly material forms the inner layer of the vest. Space between the inner and outer layers provides the pockets for the gel packs.

As contemplated, the instant invention can be utilized by lactating mothers to stimulate circulation and induce comfort for engorged breasts. The vest can be effective in post surgical environments, providing therapy to reduce bruising which may accompany mastectomies, breast implants, chest surgery, etc. Sports-persons may find the invention beneficial in treating injuries involving pulled and/or sore chest muscles. The invention has the capability for a myriad of applications involving therapy for the upper torso.

Accordingly, it is a principal object of the invention to provide a therapeutic garment for the upper torso of the human body.

It is another object of the invention to provide a therapeutic garment capable of applying warm or cold therapy for the upper torso of the human body.

It is a further object of the invention to provide a therapeutic garment for the upper torso which can be worn by either gender.

Still another object of the invention is to provide a therapeutic garment for the upper torso which is easy to put on and take off.

It is an object of the invention to provide improved elements and arrangements thereof in an apparatus for the purposes described which are inexpensive, dependable and fully effective in accomplishing their intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
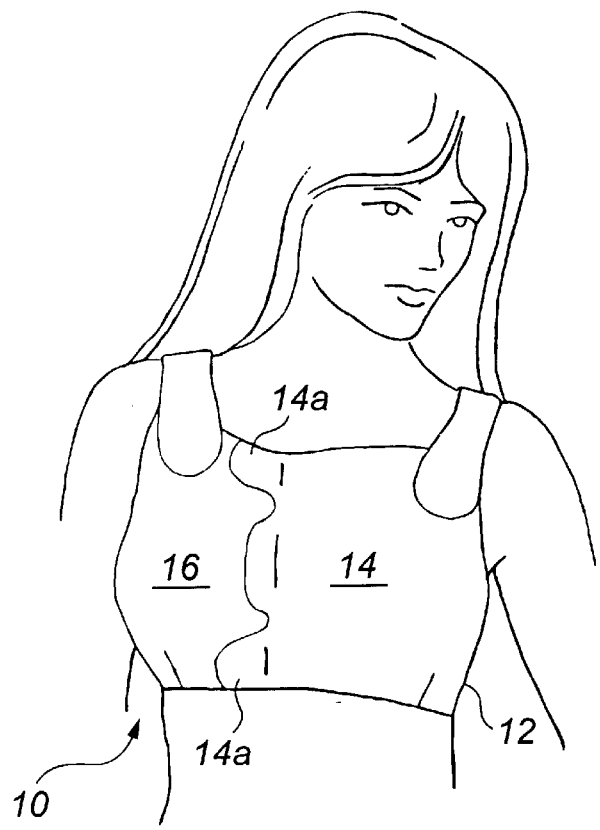
FIG. 1 is an environmental front view of a thermal vest in a closed position according to the present invention.
Figure 2:
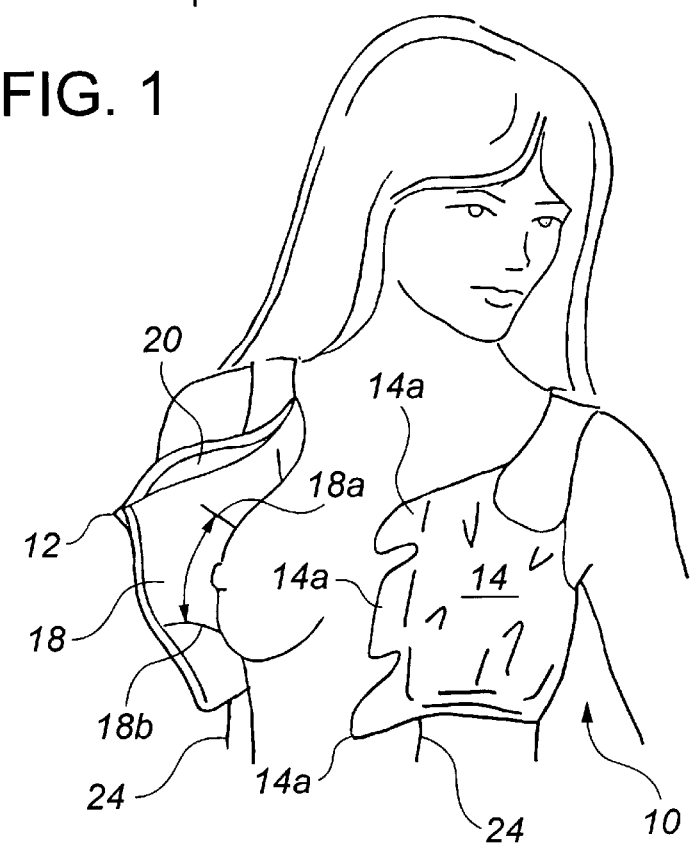
FIG. 2 is an environmental front view of a thermal vest in an open position according to the present invention.

The thermal vest of the present invention is generally indicated at 10 and includes an outer layer 12. Outer layer 12 is fabricated from a sturdy elastic material such as perforated neoprene or the like. As illustrated in FIGS. 1 and 2, vest 10 includes overlapping front panels 14 and 16. Any convenient fasteners (buttons, hooks, VELCRO, etc.) positioned on flaps 14a can be used secure the vest in its closed position (FIG. 1). In its closed position, the vest closely surrounds the upper torso. Elastic outer layer 12 functions to apply even pressure over the chest and rib cage areas.

As best seen in FIG. 2, front panels 14 and 16 are provided with a liner 18. Liner 18 will be in contact with the skin of the wearer and is made from a soft flexible material such as cotton. Pockets 20 (only one is shown) are formed between liner 18 and outer layer 12. Pockets 20 are adapted to receive and support therein conventional gel packs which will provide the heat or cold needed for therapeutic treatment. Slits 18a and 18b are formed in liner 18 to retain a breast shield 22 when the vest user is a lactating mother. Alternatively, the breast shield could be attached with double sided tape. Cinching cords 24 are provided so that the vest may be pulled tightly at the waist to ensure a snug fit.

Figure 3:
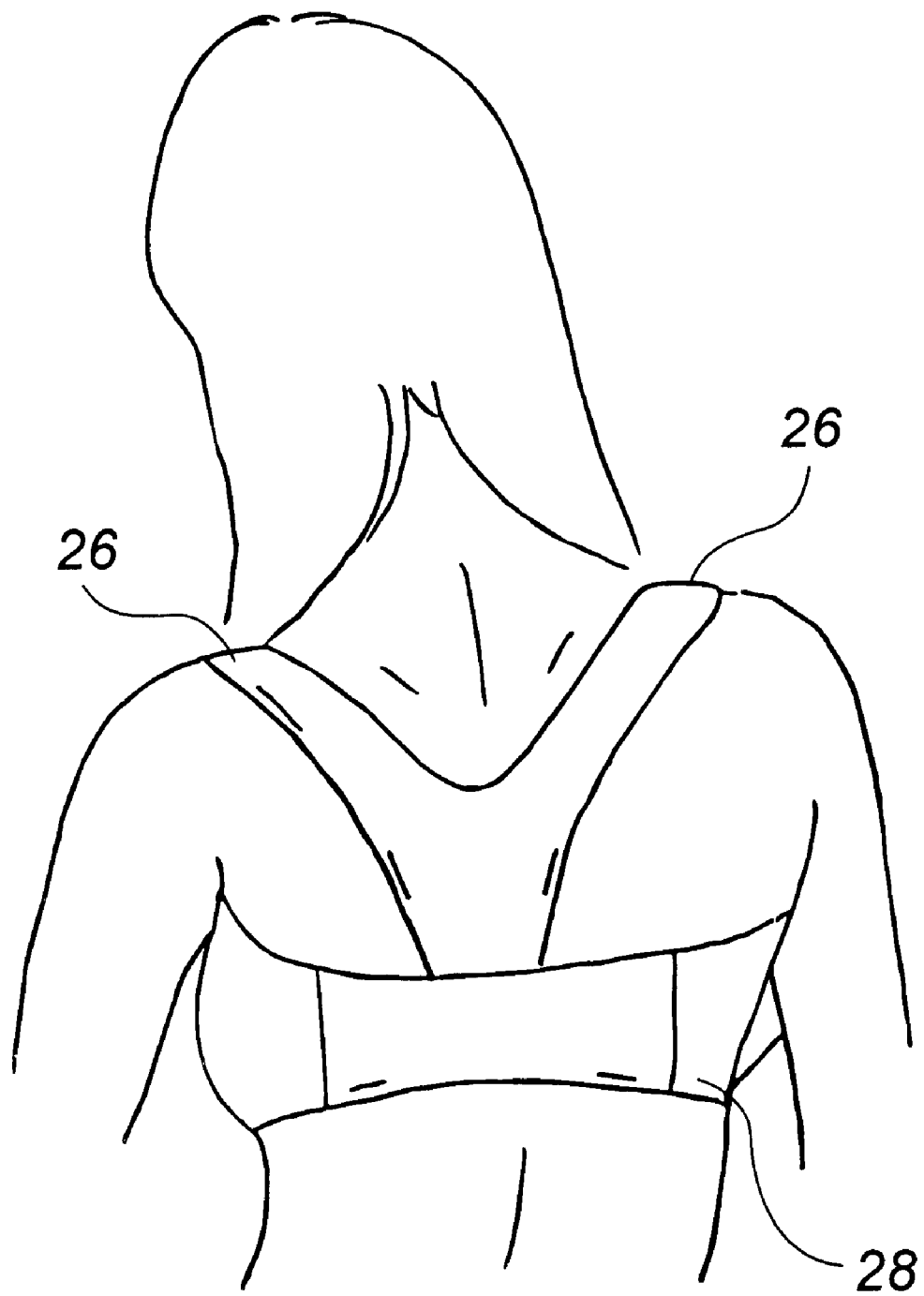
FIG. 3 is an environmental rear view of a thermal vest according to the present invention.

Shoulder straps 26 and back panel 28 (FIG. 3) are also fabricated of neoprene or like material. Straps 26 may be adjustable to accommodate a wide range of sizes. Straps 26 and back 28 may be lined for comfort if desired.

The vest as described above, can easily be manufactured in a one piece die cut configuration. The instant invention presents an effective support for large breasts while also supporting gel packs. The vest is easy to put on and is simplistic in its use.

It is to be understood that the present invention is not limited to the sole embodiment described above, but encompasses any and all embodiments within the scope of the following claims.

We claim:

1. A therapeutic garment configured to conform to a human's upper torso, said garment comprising:

a first front panel having an inner surface;

a second front panel having an inner surface;

a back panel;

said first front panel, said second front panel, and said back panel fabricated of elastic material;

a first shoulder strap having a first end connected to said back panel and a second end connected to said first front panel;

a second shoulder strap having a first end connected to said back panel and a second end connected to said second front panel;

a cotton liner disposed on the inner surface of each said first front panel and said second front panel, each said cotton liner defining a pocket adapted to retain a gel pack therein;

means for detachably fastening said first front panel to said second front panel; and a pair of slits formed in each said cotton liner, said pair of slits adapted to retain a breast shield.

2. The therapeutic garment as defined in claim 1, wherein said elastic material is perforated neoprene.

3. The therapeutic garment as defined in claim 1, wherein said means for detachably fastening said first front panel to said second front panel include flaps on said first front panel.

4. The therapeutic garment as defined in claim 3, wherein fasteners are disposed on said flaps.

5. The therapeutic garment as defined in claim 1, further including a breast shield disposed in each said pair of slits.

* * * * *